United States Patent [19]

Hargis et al.

[11] 4,072,732

[45] Feb. 7, 1978

[54] CONVERSION OF METHANOL AND DIMETHYL ETHER TO $C_2$-$C_6$ MONOOLEFINS USING A PARTIALLY HYDRATED ZIRCONIUM SULFATE CATALYST

[75] Inventors: Duane C. Hargis, Southfield; Lawrence J. Kehoe, Huntington Woods, both of Mich.

[73] Assignee: Ethyl Corporation, Richmond, Va.

[21] Appl. No.: 672,846

[22] Filed: Apr. 2, 1976

[51] Int. Cl.$^2$ ............................................... C07C 1/20
[52] U.S. Cl. ................................ 260/682; 260/677 R; 260/681; 260/668 R
[58] Field of Search ................... 260/682, 668 R, 681, 260/677 R

[56] References Cited

U.S. PATENT DOCUMENTS

| | | | |
|---|---|---|---|
| 1,895,529 | 1/1933 | Taylor et al. | 260/682 |
| 1,914,722 | 6/1933 | Jaeger | 260/682 |
| 2,129,732 | 9/1938 | Fulton et al. | 260/682 |
| 2,456,584 | 12/1948 | Gorin et al. | 260/668 R |
| 3,082,272 | 3/1963 | Long | 260/682 |
| 3,240,697 | 3/1966 | Miale et al. | 260/682 |
| 3,845,155 | 10/1974 | Heckelsberg | 260/682 |

Primary Examiner—Veronica O'Keefe
Attorney, Agent, or Firm—Donald L. Johnson; Robert A. Linn; Willard G. Montgomery

[57] ABSTRACT

Catalytic process for converting dimethyl ether and methanol to higher hydrocarbons, comprising contacting the dimethyl ether and/or methanol with an alumina, silica or zirconia-supported zirconium sulfate catalyst, at an elevated temperature.

6 Claims, No Drawings

4,072,732

CONVERSION OF METHANOL AND DIMETHYL ETHER TO $C_2$-$C_6$ MONOOLEFINS USING A PARTIALLY HYDRATED ZIRCONIUM SULFATE CATALYST

BACKGROUND OF THE INVENTION

The present invention is directed to a novel catalytic process for converting dimethyl ether and methanol to hydrocarbons.

The conversion of dimethyl ether in the presence of a predominantly isobutane diluent to a mixture of normally liquid hydrocarbons predominantly of the isoparaffinic and aromatic types using synthetic alumina, synthetic alumina-silica, or acid-leached alumina catalysts is known (see U.S. Pat. No. 2,456,584). It is also known that tertiary monoolefins can be prepared from the decomposition of tertiary ethers in the presence of a catalyst comprising a carrier material, e.g., alumina, having a specific surface area of at least 25 $m^2/g$ combined with a weakly acidic component, e.g., a weakly acidic aluminum sulfate (see British Pat. No. 1,173,128).

Conversion of methanol and dimethyl ether by contact with a catalyst comprising a crystalline alumina silicate zeolite is disclosed in U.S. Pat. No. 3,911,041.

Applicants have discovered that dimethyl ether and methanol can be converted to higher hydrocarbons at elevated temperatures by contacting either or both of them with a catalyst comprising zirconium sulfate on a support selected from alumina, zirconia, and silica.

SUMMARY OF THE INVENTION

Dimethyl ether and methanol are converted to higher hydrocarbons by contacting either or both of them at an elevated temperature with a catalyst comprising zirconium sulfate supported on alumina, silica, or zirconia.

DESCRIPTION OF THE PREFERRED EMBODIMENTS

This invention is broadly directed to conversion of dimethyl ether and methanol to higher hydrocarbons; that is, to hydrocarbons containing two or more carbon atoms. Methanol alone or dimethyl ether alone may be converted to higher carbon number compounds by contact with a catalyst. However, a mixed feed of methanol and dimethyl ether may also be employed. while not wishing to be bound by any theory, it is postulated that, where methanol is used it reacts in the presence of the catalyst to form first dimethyl ether and the higher carbon number compounds formed thereafter are those resulting from the reaction of the dimethyl ether in the presence of the catalyst.

In accordance with the present invention one embodiment resides in a process comprising converting dimethyl ether, $CH_3$—O—$CH_3$, by contacting it with a silica, alumina or zirconia-supported zirconium sulfate catalyst under reaction conditions. Generally, the reaction conditions employed are not critical, and may be varied to accomplish the desired result. The reaction conditions are not truly independent variables, but are somewhat interdependent. In general, however, the reaction temperature is one of the more important reaction conditions and should be high enough for the reaction, i.e., the conversion of dimethyl ether or methanol to higher hydrocarbons, to occur. Thus, for example, a process conducted at low temperatures and high space velocities may result in a lower conversion rate to higher hydrocarbons than a process conducted at higher temperatures and lower space velocities. Furthermore, the reaction conditions can depend on catalyst strength, catalyst concentration, reaction vessel type, catalyst supports, and other like conditions.

Thus, in a general aspect, the present invention contemplates reaction conditions selected from the following variables and ranges:

(1) temperature - from about 100° to about 1,000° C. with from about 250° C. to about 600° C. being preferred, and with from about 200° to about 400° C. being more preferred;

(2) gaseous space velocity - the gaseous space velocity being defined as volume of gas passed over volume of catalyst per hour — of from about 0.5 to about 20,000, with from about 1 to about 10,000 being preferred, and with from about 10 to about 1,000 being more preferred;

(3) pressure - the pressure used can vary from subatmospheric to atmospheric to superatmospheric, with atmospheric pressures and superatmospheric pressures up to about 1000 p.s.i.g. being preferred.

The above values are generally not, except for the temperature, very critical and the process of the present invention can be conducted under conditions outside the aforecited ranges.

Although not bound by any theory, it is believed that while generally the zirconium sulfate is the active catalyst the type of support used contributes to some extent towards the selectivity of the product mix. Thus, the zirconium sulfate may be unsupported or it may be impregnated on a suitable support. In a preferred embodiment the zirconium sulfate is supported on alumina, preferably γ-alumina, silica, and zirconia supports. These supports are crystalline in structure and are generally commercially available.

The reaction of the dimethyl ether or methanol is preferably carried out in the vapor phase.

The dimethyl ether or methanol reacts in the presence of the catalyst and the products obtained result solely from reaction of the reactant with itself; thus the presence of a co-reactant is not required.

Fixed bed or movable bed operation may be employed. Preferably, a fixed bed operation is used. The bed may consist of unsupported zirconium sulfate or supported zirconium sulfate. Preferred supports for the zirconium sulfate are alumina, preferably γ-alumina, silica, and zirconia.

It is generally preferable to activate the catalyst by heating it in order to partially dehydrate it. Preferably the catalyst is dehydrated until there is generally less than one mole of $H_2O$ per mole of $Zr(SO_4)_2$. This activation is accomplished by heating the catalyst until the desired dehydration occurs. The activation times, temperatures, and pressures are not critical and can vary over wide ranges. The activation conditions should be such, however, that they are sufficient to dehydrate the catalyst so that there generally remains about one mole or less than one mole of water per mole of $Zr(SO_4)_2$, but insufficient to completely dehydrate the $Zr(SO_4)_2$, i.e., drive off all the water of hydration. Generally, activation temperatures of from about 200° to about 400° C. are used. The time that the catalyst is heated is dependent to a degree upon the temperature. Thus, at higher temperatures the time necessary for activation decreases while with a decrease in temperature there is an increase in the time necessary to achieve activation of the catalyst. Generally, the time periods range from about 1 to about 5 hours. The pressures at which activation is carried out are not critical and can be subatmospheric, atmospheric, or superatmospheric. Subatmospheric pressures are preferred as they tend to speed up the activation without requiring the use of overly high temperatures.

If a supported zirconium-sulfate catalyst is used it can be made by first preparing an aqueous solution of zirconium sulfate and then by impregnating the support with the solution to achieve the desired concentration of zirconium sulfate on the support. While the amount of zirconium sulfate on the support can vary over wide ranges it is generally preferred to have a support which contains from about 1 to about 60 weight percent of partially hydrated zirconium sulfate, and more preferably from about 5 to about 20 weight percent of partially hydrated zirconium sulfate.

In the preparation of the supported zirconium sulfate the support with the hydrated zirconium sulfate thereon is activated by heating until generally about one or less than one mole of water of hydration remains per mole of $Zr(SO_4)_2$. The activating conditions are those as described above.

In the following table are set forth the results for various runs of converting dimethyl ether to higher hydrocarbons according to the present invention. The space velocities in these runs were about 100. In the following table $$\% \text{ conversion} = \frac{\text{mole \% dimethyl ether in reacted gas}}{100} \times 100$$

and $$\% \text{ yield} = \frac{\text{mole \% product}}{\% \text{ dimethyl ether converted}} \times 100;$$

and $C_1$ is methane, $C_2$ is ethylene, $C_3$ is propylene, $C_4$ is butene, $C_5$ is pentene, and $C_6$ is hexene.

TABLE

| Catalyst | Temp. °C. | % Conversion | % Yield |||||| 
|---|---|---|---|---|---|---|---|---|
| | | | $C_1$ | $C_2$ | $C_3$ | $C_4$ | $C_5$ | $C_6$ |
| Unsupported zirconium sulfate | 330 | 13.5 | 26.4 | 24.4 | 21.5 | 10.0 | 9.1 | 1.9 |
| 10 wt. % zirconium sulfate on silica | 315–335 | 7.2 | 11.5 | 28.9 | 20.1 | 18.0 | 11.7 | 4.5 |
| 10 wt. % zirconium sulfate on γ-alumina | 330–340 | 21.2 | 24.2 | 25.6 | 16.5 | 13.5 | 8.5 | 3.5 |
| 10 wt. % zirconium sulfate on zirconia | 295 | 12.7 | 5.7 | 31.0 | 22.8 | 18.6 | 11.8 | 5.5 |

It can be seen from the table that zirconium sulfate supported on zirconia gives significantly lower methane yields than zirconium sulfate on silica or γ-alumina supports or unsupported zirconium sulfate. Also the yield of ethylene with the zirconia supported zirconium sulfate is higher than with silica or γ-alumina supported zirconium sulfate or unsupported zirconium sulfate.

Thus, a preferred embodiment of the present invention is a process for the conversion of dimethyl ether comprising contacting said dimethyl ether with a catalyst comprising a catalyst comprising partially dehydrated zirconium sulfate supported on a crystalline zirconia support.

Results similar to those reported above can be achieved using methanol or a mixture of methanol and dimethyl ether.

We claim:

1. A process for the conversion of a reactant selected from the class consisting of methanol and dimethyl ether to $C_2$-$C_6$ monoolefin, said process comprising contacting said reactant with a partially hydrated zirconium sulfate catalyst at a temperature within the range of about 200° C. to about 400° C.

2. The process of claim 1 wherein said zirconium sulfate catalyst contains an amount of water of hydration sufficient to effect catalytic activity of the catalyst, but not more than about one mole of water of hydration per mole of $Zr(SO_4)_2$.

3. The process of claim 2 wherein said zirconium sulfate is supported on a support selected from the class consisting of crystalline γ-alumina, crystalline silica, and crystalline zirconia.

4. The process of claim 3 wherein said support is crystalline γ-alumina.

5. The process of claim 3 wherein said support is crystalline silica.

6. The process of claim 3 wherein said support is crystalline zirconia.

* * * * *